United States Patent [19]

Murabayashi et al.

[11] Patent Number: 4,877,816

[45] Date of Patent: Oct. 31, 1989

[54] DEODORANT AND ANTIBACTERIAL FOAMED POLYMER AND SHEET

[75] Inventors: Katsuyoshi Murabayashi, Sakai; Katsuyoshi Mitani, Amagasaki, both of Japan

[73] Assignee: Daicel Chemical Industries, Ltd., Osaka, Japan

[21] Appl. No.: 136,778

[22] Filed: Dec. 22, 1987

[30] Foreign Application Priority Data

Dec. 24, 1986 [JP] Japan ................. 61-313866
Dec. 24, 1986 [JP] Japan ................. 61-313867

[51] Int. Cl.$^4$ .............................. C08J 9/00
[52] U.S. Cl. ..................... 521/92; 428/286; 428/423.1; 428/423.7; 521/122; 521/143; 521/146
[58] Field of Search ............... 521/92, 122, 143, 146

[56] References Cited

U.S. PATENT DOCUMENTS

| | | | |
|---|---|---|---|
| 3,127,312 | 3/1964 | Boyer | 521/113 |
| 3,912,666 | 10/1975 | Spitzer et al. | 521/78 |
| 3,912,667 | 10/1975 | Spitzer et al. | 521/149 |
| 4,226,944 | 10/1980 | Stone et al. | 521/160 |
| 4,339,550 | 7/1982 | Palinczar et al. | 521/121 |
| 4,631,297 | 12/1986 | Battice et al. | 521/78 |

*Primary Examiner*—Morton Foelak
*Attorney, Agent, or Firm*—Birch, Stewart, Kolasch & Birch

[57] ABSTRACT

A foamed polymer composition comprises a foamed polymer, fine particles of a deodorant and fine particles of an antibacterial agent. The composition is usable in the form of a film. It provides the film with deodorant and antibacterial efffects even after the film has been washed.

9 Claims, No Drawings

DEODORANT AND ANTIBACTERIAL FOAMED POLYMER AND SHEET

FIELD OF THE INVENTION

The present invention relates to foams having deodorant and anti-organism properties such as anti-bacterial and mildew resistance properties. These foams are usable for multi-purposes.

The present invention also relates to a water-non-permeable deodorant, anti-bacterial sheet, which is obtained by laminating the foams with a fiber sheet. The sheet maintains deodorant and anti-bacterial properties even after having been washed. It can be used for various purposes.

PRIOR ART

A patent which discloses a plastic film containing a ferric compound and ascorbic acid particles exhibits a deodorant property and is useful as a food wrapping material was recently published. (Japanese Patent Provisional Publication No. 61(1986)-60732). In the above mentioned Provisional Publication an example of a polypropylene film having a thickness of 50 microns and is prepared by an inflation method is described.

Deodorant particles are partially exposed to the atmosphere at the surface of the above mentioned film, but primarily the particles are enclosed in the film and therefore the particles would absorb odorous gases such as ammonia through the thin polypropylene layers which are positioned between the particles and the surface of the film.

Thick plastic moldings having deodorant properties are not known.

However, some plastics inherently generate objectionable odors during molding operations, and some deodorant methods have been proposed to deodorize such odors. Especially in the case of foamed plastics, during a foaming process, some of these plastics generate odorous gasses such as ammonia and amine. Several patents which involve methods for odorless foaming have been applied for. (For example Japanese Patent Provisional Publication No. 59(1984)-43037). However these methods involve the removal of odors generated from the plastics themselves, and do not involve removal of odors generated from materials other than the plastics themselves.

In the case of plastic films, the thickness ranges in general from 10 to 100 microns. On the other hand in the case of high expansion ratio foam plastics, the thickness of foam shells lie in the range of several microns and is thinner than that of the above mentioned films.

The present inventors considered that, plastic compositions with the deodorant property could be obtained and the deodorant property of such compositions might be superior to that of the films, if deodorant particles could be contained in high expansion ratio from plastics by a suitable method. Similarly, if particles which have anti-organism properties such as an anti-bacterial property and a mildew resistance property could be contained together with deodorant particles in high expansion ratio plastics, the plastic compositions resulting therefrom would exhibit both the above mentioned deodorant and anti-organism properties.

To attain the purpose of the present invention, the materials to be added in plastics should not have an adverse effect on the inherent performance of the plastics such as strength and color and also should not have an adverse effect on the foaming property. The particles comprising ferric compound and ascorbic acid, described in the above mentioned Japanese Patent Provisional Publication No. 61(1986)-60732, have an adverse effect on the foaming property and, when a cationic, organism activity preventing agent is used, the effect of such an agent is reduced.

Deodorant, anti-bacterial woven fabrics and non-woven fabrics to which deodorant agents and anti-bacterial agents are applied by conventional methods, such as dipping, sandwiching, coating and the like are well known, but such woven fabric or non-woven fabric which retains deodorant and anti-bacterial properties after washing have been not known.

SUMMARY OF THE INVENTION

The present inventors successfully obtained the foamed plastics of the present invention by using the combination of a deodorant agent and organism acitivity preventing agent, both of which are insoluble or difficulty soluble in water.

The present inventors in proceeding with the research found that a foam, prepared by mixing a selected deodorant agent and anti-bacterial agent under selected conditions in an expandable urethane material which forms closed cells, followed by foaming the mixture exhibits deodorant and anti-bacterial properties. The present inventors also found that a laminated sheet which comprises a laminated sheet of said foamed polyurethane and a fiber sheet, such as a woven fabric, or non-woven fabric, is nonpervious to water and air and had various functions. Therefore it can be used for multi-purposes. Thus the present invention was attained.

The present invention relates to deodorant, anti-bacterial foamed plastics which contain deodorant and anti-bacterial particles.

A foamed polymer composition according to the present invention comprises a foamed polymer, fine particles of a deodorant and fine particles of an antibacterial agent.

The composition preferably comprises 100 parts by weight of the foamed polymer, 3 to 30 parts by weight of the deodorant and 0.2 to 2 parts by weight of the antibacterial agent. It is preferable that the fine particles of the deodorant and those of the antibacterial agent have a particle which is sufficiently small in size, such that it would at least pass through a sieve having 30 mesh according to JIS. The fine particles preferably have an average size of 30 to 500 mesh, more preferably 200 to 300 mesh. The composition may be in the form of a film. The present invention also provides a sheet laminate which comprises a fiber sheet and a sheet of the foamed polymer composition as defined above, which is laminated on the fiber sheet.

As the deodorant agent used according to the present invention, reaction type deodorant agents, especially inorganic deodorant agents, are suitably used because such deodorant agents react rapidly with odorous gas. Deodorant agent and anti-bacterial agent are preferably insoluble or difficulty soluble in water. Basic zinc carbonate and ferrous sulfate monohydrate are examples of the deodorant agent and N(fluorodichloromethylthio)phthalimide and N,N-dimethyl-N'-phenyl-N'-(fluorodichloromethylthio)sulfamide are examples of the anti-bacterial agent, which are effectively used. Both the deodorant agent and anti-bacterial agent are essentially in the form of fine particles. The particles preferably will at least pass through a 30 mesh screen. Such deodorant and anti-bacterial agents are added to an expandable plastic material, along with the required compound materials, such as a foaming agent and a filler to form the composition which is foamed under the usual conditions to obtain the foamed plastics.

The polymer to be used in the present invention includes polyurethane, polyethylene, polypropylene and polystyrene.

3 to 30 g of a deodorant agent and 0.2 to 2 g of an anti-bacterial agent are preferably added to 100 g of a plastic resin solid. If the quantities are less than any one of these values, the remarkable effects of the foamed composition of the present invention are not obtained. On the other hand if the quantities are more than any one of these values, the expandability of the plastic would tend to deteriorate. The expansion ratio is usually not affected by addition of the agents within the above mentioned range, but tends to decrease with addition of the Therefore, it is recommended that production be carried out after a small scale test.

Foams of the present invention, regardless of whether they are closed cell foam or open cell foam, are excellent for the removal of odors in the atmosphere and the effect of the anti-bacterial property and the mildew resistance, continues for a long period of time.

The present invention relates to a deodorant anti-bacterial sheet comprising a laminated fiber sheet and foamed sheet containing the deodorant particles and anti-bacterial particles which maintains deodorant and anti-bacterial properties even after washing. 3 to 30 g/m² based on the sheet product of a deodorant agent and 0.2 to 2 g/m² based on the sheet product of an anti-bacterial agent are suitably used.

To form a foamed urethane sheet, deodorant particles and anti-bacterial particles may be mixed in a raw material composition containing a foaming agent and may be foamed by a conventional method. The above mentioned additives affect on the expansion ratio depends on the situation. Therefore, it is desirable that after the preliminary experiment has been conducted, the production thereof is carried out. But usually expansion ratio is hardly affected within the above mentioned addition ranges of additives.

Foaming may be conveniently carried out by dry foaming. A foam sheet may be obtained by foaming in a sheet form or by slicing a bulk foam. Any fiber sheet such as woven fabrics, non-woven fabrics and knit fabrics may be used.

Foam plastics of the present invention having deodorant and anti-bacterial effects, are useful for making other articles deodorant and anti-bacterial. Especially the foamed plastic of the present invention is useful, for making an elastic foam such as a polyurethane foam, with high expansion ratio.

The sheet material of the present invention is unexpectedly improved in heat-retaining property and cushion property, and can be subjected suitably to various processes such as cutting, adhesion, and sewing. Thus the sheet material is used for a wide range of applications such as textile goods, interiors, and synthetic leathers, which are made deodorant and anti-bacterial by the use of the sheet. Especially, the sheet of the present invention is effectively used for materials such a diaper cover and a slipper because the sheet retains deodorant and anti-bacterial properties even after repeated washing.

The sheet material of the present invention causes no rash when the sheet material is used for medical applications because the deodorant agent and anti-bacterial agent itself does not contact directly with the skin.

EXAMPLE

The present invention will be described referring to the examples hereinunder, but this invention will by no means be restricted by these examples.

Example 1

Basic zinc carbonate and N-(fluorodichloromethylthio)phthalamide (250 mesh pass) were used as the deodorant agent and the anti-bacterial agent, respectively, mixed with urethane resin according to the recipe shown below. The mixture was cast on a releasing paper followed by dry foaming to prepare a foam polyurethane sheet containing the deodorant agent and anti-bacterial agent.

| | |
|---|---|
| Urethane resin (UF-1N,SEIKO KASEI) | 100 parts by weight |
| Foaming agent (FAD-13,SEIKO KASEI) | 3 parts by weight |
| Cross-linking agent (FAD-11,SEIKO KASEI) | 2 parts by weight |
| Filler (FAD-12,SEIKO KASEI) | 2 parts by weight |
| Foam controlling agent (FAD-10,SEIKO KASEI) | 1 parts by weight |
| Deodorant agent | 20 parts by weight |
| Anti-bacterial agent | 1 parts by weight |
| Solvent (dimethylformamide) | 10 parts by weight |
| Total | 139 parts by weight |

The procedure of preparation is described in detail in the following. The above mentioned ingredients of prescribed amounts were mixed well for 30 min in a dissolver to form a mixture with a viscosity of approximately 10,000 cps, the mixture was cast with a thickness of 0.17 mm on a releasing paper followed by preheating at 120° C. for 1 min and curing at 130° C. for 2 min to foam the polyurethane. The thickness of the obtained sheet was 0.5 mm. The foamed polyurethane sheet contains closed cells.

Separately a non-foamed urethane film was prepared under the conditions described below.

| | |
|---|---|
| Urethane resin (KURISUBON7600, DAINIPPON INK & CHEMICALS, INC) | 100 parts by weight |
| Dimethylformamide | 20 parts by weight |
| Methylethylketone | 30 parts by weight |
| Total | 150 parts by weight |

The above mentioned ingredients were mixed well to obtain a solution with a viscosity of 1500 cps containing 20% of solid, the mixture was cast with a thickness of 50 microns on a releasing paper followed by drying at 110° C. for 1 min to obtain a film with a thickness of 10 microns.

Then the above mentioned foamed polyurethane sheet and non-foamed urethane film were bonded with an adhesive joining both free surfaces of the sheet and film. Bonding was carried out according to a procedure described hereinunder. Polyurethane adhesive (KURISUBON4010, DAINIPPON INK & CHEMICALS INC. curing agent was added) was diluted with a solvent (dimethylformamide, ethylacetate) to prepare a solution with a solid content of approximately 40%, the solution was coated on the free upper surface of the foamed urethane sheet and dried at 100° C. for 1 min, then the film was put on the surface and pressed at 100° C. under the pressure of 40 kg/cm², and allowed to stand for 24 hr.

The urethane sheet obtained according to the procedure of Example 1 contains approximately 20 g of basic zinc carbonate and approximately 1 g of N(fluorodichloromethylthio)phthalimide per 1 squere meter. The deodorant and anti-bacterial mildew resistant performances of obtained urethane sheet were measured by methods described below.

Ammonia gas ($NH_3$):

A piece of the sheet (size 11 cm×18 cm) is put in a desiccator with a volume of 6.3 liter which was previously filled with ammonia gas with an initial adjusted concentration ($C_0$) of 85 to 105 ppm, the ammonia gas concentration (C) is measured after 4 hr, and $C/C_0$ is determined.

Hydrogen sulfide gas ($H_2S$):

A piece of the sheet (size 11 cm×18 cm) is put in a desiccator with a volume of 6.3 liter which was previously filled with hydrogen sulfide gas with an initial adjusted concentration ($C_0$) of 30 to 40 ppm, the hydrogen sulfide gas concentration (C) is measured after 4 hr, and $C/C_0$ is determined.

Anti-bacterial property:

*Staphylococcus aureus* and *Escherichia coli* are used. The test is carried out according to AATCC test method 100-1981. A piece of the sheet with a size 3 cm×3 cm is used, the test is repeated three times and the result is represented by the average. A sample sheet is put in a 100 mL Erlenmeyer flask followed by sterilization, 0.3 ml of test bacteria solution which contains approximately $10^5$ bacteria/ml is dropped and inoculated evenly followed by incubation at a room temperature for 6 hr. After incubation live bacteria in the sample are dispersed in a sterilized physiological salt solution containing 0.1% tritonX-100. The dispersion is diluted and put into a Petri dish and, after preparation of a plate with tryptone-D agar medium the bacteria are incubated at 35° C. for 48 hr. After incubation number of colony which appears in the Petri dish is counted, and the number is compared with a number which is separately determined for live bacteria immedeately after inoculation. The result is represented by the reduction ratio.

Mildew resistance:

The test is carried out according to JIS Z2911 test method of textile products for mildew resistance, that is, mildew spore suspension of alpelgilsflabus ATCC 9643 is sprayed to inoculate, and incubated at 30° C. for 4 weeks. Results of measurement is shown in Table 1.

TABLE 1

| Deodorant performance $C/C_0$ | | Anti-bacteria (reduction) | | Mildew resistance |
|---|---|---|---|---|
| Ammonia | hydrogen sulfide | *staphylococci* | coliform *bacilli* | |
| 0.10 | 0.00 | 99.9 | 99.9 | not grow |

Example 2

Basic zinc carbonate and N-(fluorodichloromethylthio)phthalimide (200 mesh pass) to work as a deodorant agent and an anti-bacterial agent, respectively, were mixed with urethane resin according to the recipe described below, then the mixture was cast on a releasing paper followed by dry foaming to prepare foamed polyurethane sheet containing the deodorant agent and anti-bacterial agent.

| | | |
|---|---|---|
| Urethane resin (UF-3A,SEIKO KASEI) | 100 | parts by weight |
| Filler (FAD-30,SEIKO KASEI) | 10 | parts by weight |
| Foaming agent (FAD-31,SEIKO KASEI) | 1 | parts by weight |
| Deodorant agent | 13 | parts by weight |
| Anti-bacterial agent | 0.7 | parts by weight |
| Total | 124.7 | parts by weight |

The procedure of preparation is described in detail in the following. The above mentioned ingredients of prescribed amounts were mixed well for 30 min in a dissolver to form a mixture, the mixture was cast with a thickness of 0.15 mm on a releasing paper followed by curing at 130° C. for 2 min to foam the polyurethane. The foamed polyurethane sheet contains closed cells and the thickness of the obtained sheet was 0.5 mm. The urethane sheet contains approximately 10 g of basic zinc carbonate and approximately 0.8 g of N(fluorodichloromethylthio)phthalamide per 1 square meter. Then on the free surface of the above mentioned foamed urethane sheet a polyester knit fabric (basis weight of 100 g/m²) was laminated using conditions described hereinunder.

Adhesive: polyurethane adhesive, diluted with dimethylformamide/ethyl acetate to a solid content of 38%.

Thickness: approximately 100 microns, on the polyurethane sheet, drying for 1 min.

Lamination: putting a knit fabric on the polyurethane sheet, pressing at 100° C. under a pressure of 40 kg, and aging for 24 hr.

The laminate obtained above was examined in view of the deodorant and antibacterial properties in the same way as shown in Example 1.

The measurement was carried out on the original sheet and also on washed sheet. The washing condition were described hereinunder.

Washing test: Washing condition in an electric washing machine

Detergent: Neutral detergent 10 g/5 liter of water.
Washing time: 5 min.
Dehydration time: 1 min.
Rinsing time: 8 min.
Dehydration time: 2 min.

Results of measurement are shown in Table 2.

TABLE 2

| | Deodorant performance $C/C_0$ | | Anti-bacterial property (Reduction ratio) | |
|---|---|---|---|---|
| | Ammonia | Hydrogen sulfide | *Staphylococcus Aureus* | *Escherichia Coli* |
| Original sheet | 0.18 | 0.00 | 99.9 | 99.9 |
| After 10 wash | 0.30 | 0.04 | — | — |
| After 30 wash | 0.51 | 0.29 | 99.8 | 99.8 |

Laminated sheet obtained in Example 2 exhibited excellent deodorant performance in using a diaper cover.

Example 3

A laminated sheet comprising a non-foamed urethane film/foamed urethane sheet/woven fabric or non-woven fabric was prepared through a procedure described hereinunder. At first a non-foamed urethane film was formed on a releasing paper.

| | |
|---|---|
| Urethane resin (KURISUBON SC-7006, DAINIPPON INK & CHEMICALS, INC.) | 100 parts by weight |
| Solvent (dimethylformamide) | 20 parts by weight |
| Solvent (ethylacetate) | 30 parts by weight |
| Yellow pigment | 10 parts by weight |
| Total | 160 parts by weight |

The above mentioned ingredients (20% solid) was cast with a thickness of 100 microns and dried at 100° C. for 1 min to form a non-foamed urethane film.

Then, urethane resin prepared according to the recipe described hereinunder using the same deodorant agent and anti-bacterial agent was cast with a thickness of approximately 0.3 mm on the above mentioned film followed by preheating at 120° C. for 1 min and curing at 130° C. for 2 min to foam the urethane.

| | |
|---|---|
| Urethane resin (UF-1N,SEIKO KASEI) | 100 parts by weight |
| Foaming agent (FAD-13,SEIKO KASEI) | 3 parts by weight |
| Cross linking agent (FAD-11,SEIKO KASEI) | 2 parts by weight |
| Filler (FAD-12,SEIKO KASEI) | 2 parts by weight |
| Foam controlling agent (FAD-10,SEIKO KASEI | 1 parts by weight |
| Deodorant agent | 20 parts by weight |
| Anti-bacterial agent | 1 parts by weight |
| Solvant (dimethylformamide) | 10 parts by weight |
| Total | 139 parts by weight |

The thickness of the obtained foam urethane sheet was 0.8 mm. On the obtained urethane sheet, a polyester non-woven fabric (basis weight of 25 g/m$^2$) was laminated according to the method of Example 2, a laminated sheet comprising urethane film foamed urethane sheet/non-woven fabric was obtained.

The obtained laminated sheet was used for the material of a bag, thus a bag made of synthetic leather with excellent deodorant performance was obtained.

What is claimed is:

1. A foamed polymer composition which comprises 100 parts by weight of a foamed polymer which comprises a foamed polyurethane, polyethylene, polypropylene or polystyrene, 3 to 30 parts by weight of fine particles of a deodorant which comprises basic zinc carbonate or ferrous sulfate monohydrate and 0.2 to 2 parts by weight of fine particles of an antibacterial agent which comprises N-(fluorodichloromethylthio)-phthalamide or N,N-dimethyl-N'-phenyl-N'-(fluorodichloromethylthio)-sulfamide, wherein the deodorant and the antibacterial agent fine particles are insoluble or difficulty soluble in water and wherein the fine particles of the deodorant and the antibacterial are sufficiently small in size, such that said fine particles will at least pass through a sieve having 30 mesh according to JIS.

2. The foamed polymer composition as claimed in claim 1, which is in the form of a film.

3. A sheet assembly which comprises a fiber sheet and a sheet of the foamed polymer composition as defined in claim 1, laminated on the fiber sheet.

4. The foamed polymer composition as claimed in claim 1, in which the fine particles of the deodorant and the antibacterial have an average size of 30 to 500 mesh.

5. The foamed polymer composition as claimed in claim 1, in which the fine particles of the deodorant and the antibacterial have an average size of 200 to 300 mesh.

6. The foamed polymer composition as claimed in claim 1, in which the foamed polymer is a foamed polyurethane.

7. The foamed polymer composition as claimed in claim 1, in which the foamed polymer is a formed polyurethane.

8. The foamed polymer composition as claimed in claim 1, which is in the form of a film.

9. The foamed polymer composition as claimed in claim 7, which is in the form of a film.

* * * * *